US012211620B2

(12) United States Patent
Devore et al.

(10) Patent No.: US 12,211,620 B2
(45) Date of Patent: Jan. 28, 2025

(54) MACHINE LEARNING MODELS FOR VEHICLE ACCIDENT POTENTIAL INJURY DETECTION

(71) Applicant: State Farm Mutual Automobile Insurance Company, Bloomington, IL (US)

(72) Inventors: Justin Devore, Atlanta, IL (US); Sateesh K Nallamothu, Normal, IL (US); Dayne Dalpoas, Delavan, IL (US); Ruth Anne Grosskopf, Bloomington, IL (US); Jason Beckman, Bloomington, IL (US); Kathleen Cordiner, Sun Lakes, AZ (US); Jennifer Megargell, Bloomington, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 254 days.

(21) Appl. No.: 17/685,683

(22) Filed: Mar. 3, 2022

(65) Prior Publication Data
US 2023/0282350 A1    Sep. 7, 2023

(51) Int. Cl.
*G16H 50/20* (2018.01)
*G06N 7/01* (2023.01)
*G06N 20/00* (2019.01)

(52) U.S. Cl.
CPC .............. *G16H 50/20* (2018.01); *G06N 7/01* (2023.01); *G06N 20/00* (2019.01)

(58) Field of Classification Search
None
See application file for complete search history.

(56) References Cited

U.S. PATENT DOCUMENTS 5,529,041 A * 6/1996 Andrews ................ G01M 15/11
  123/436
9,675,719 B2 * 6/2017 Kirkwold .................. A61L 2/10
(Continued)

OTHER PUBLICATIONS

Augenstein et al.: "Development And Validation of the Urgency Algorithm to Predict Compelling Injuries"; Jun. 4, 2001 (Year: 2001).*

(Continued)

*Primary Examiner* — John A Pauls
(74) *Attorney, Agent, or Firm* — Lee & Hayes, P.C.

(57) ABSTRACT

Techniques described herein relate to training and executing machine learning models configured to determine injury probabilities based on vehicle accident data. In some cases, a decision tree model may be constructed including various branching criteria based on particular vehicle accident data and injury ground truth data, including leaf nodes storing corresponding injury probabilities. A model execution component may execute the trained models to determine the probability of potential injuries associated with vehicle accidents. Based on the potential injury probabilities, a vehicle accident analysis system may identify target computer systems and/or target processes to be initiated on the target systems, based on the injury probabilities. In some example, the model execution architecture may be implemented using an event-driven system and/or cloud-based data storage and services to receive, store, and process data events associated with individual vehicle accidents.

20 Claims, 8 Drawing Sheets

(56) References Cited

U.S. PATENT DOCUMENTS

| 2009/0048996 | A1* | 2/2009 | Bala ........................ | G06N 7/01 |
| | | | | 706/46 |
| 2020/0312063 | A1* | 10/2020 | Balakrishnan ......... | G07C 5/008 |
| 2023/0078210 | A1* | 3/2023 | Kolaxis ................. | G08B 25/12 |
| | | | | 455/404.2 |

OTHER PUBLICATIONS

Assi et al. "Predicting Crash Injury Severity with Machine Learning Algorithm Synergized with Clustering Technique: A Promising Protocol"; Jul. 30, 2020 (Year: 2020).*

Champion et al.: "Automatic Crash Notification and the Urgency Algorithm Its History, Value and Use"; Topics in Emergency Medicine/Apr.-Jun. 2004, vol. 26, No. 2, pp. 143-156 (Year: 2004).*

Candefjord et al.: "On Scene Injury Severity Prediction (OSISP) machine learning algorithms for motor vehicle crash occupants in US"; Journal of Transport & Health; Jul. 21, 2021 (Year: 2021).*

Bahouth et al.: "Influence of Injury Risk Thresholds on the Performance of an Algorithm to Predict Crashes with Serious Injuries"; Oct. 14-17, 2012 (Year: 2012).*

\* cited by examiner

MACHINE LEARNING MODELS FOR VEHICLE ACCIDENT POTENTIAL INJURY DETECTION

TECHNICAL FIELD

The present disclosure relates to software development and deployment. In particular, the present disclosure describes techniques for generating and training cloud-based machine learning models, and event systems used to trigger execution of the models.

BACKGROUND

When accidents occur for vehicles in a driving environment, it can be valuable for law enforcement, medical care providers, insurance providers, and other entities to quickly and accurately determine any potential injuries that may have resulted to passengers and/or other parties. Failures to accurately detect or predict potential injuries resulting from vehicle accidents may cause delayed medical care and increased risks of bad medical outcomes for individuals that may be injured. Additionally, failing to quickly identify injuries and potential injuries resulting from a vehicle accident can cause time delays and additional processing costs associated with completing police reports, processing insurance claims, and the like. The existing techniques for identifying injuries associated with vehicle accidents often involve time-consuming and computationally complex processes, which may be error-prone and may suffer from various other significant draw backs.

For example, existing techniques for detecting injuries resulting from vehicle accidents often require manual inspection of the accident scene and/or personal interviews with the parties involved. A party to an accident may initially report the accident to a medical provider, law enforcement organization, insurer, or the like. After reporting the accident, the reporting party may be interviewed or given a medical examination, at which point the person conducting the interview or examining the party may determine whether or not that individual is injured. However, such interviews or examinations can be difficult to conduct quickly and accurately, and may be inadequate for determining all of the potential injuries resulting from the accident. For instance, systems that rely on interviews and/or examinations with the parties to an accident may fail to take into account additional relevant data from other data sources, including statements from other parties or witnesses to the accident, police reports, vehicle telematics, and other data from third-party data sources. Existing systems that determine accident injuries based on interviews and/or examinations with the parties involved, without receiving or analyzing the relevant data from these additional data sources, may fail to accurately detect the full range of injuries and potential injuries resulting from the accident.

Complicating the analysis further is the fact that some injuries resulting from an accident may be immediately apparent, while others may be unreported, concealed, and/or otherwise unknown to the parties until long after the accident has occurred. For instance, when a party involved in an accident first reports that the accident has occurred, he or she may be unaware of any potential injuries to the other parties. Additionally, an individual may state shortly after an accident that he or she is uninjured, but may subsequently experience delayed symptoms of nausea, neck pain, or other injuries that were not present immediately after the accident. Therefore, existing techniques or systems that evaluate accident data and determine potential injuries shortly after an accident may fail to detect late-reported injuries and/or other injuries that are not immediately apparent. In contrast, systems that wait to analyze and process accident data can lead to delayed detection of potential injuries, resulting in higher-risk medical outcomes and additional time and expense when processing the accident data by law enforcement, insurance providers, etc.

Further, various types of relevant vehicle accident data can be received from the various data sources over different communication channels and/or at different times, including shortly after an accident has occurred or significantly later. Each of these data sources may provide relevant data for analyzing vehicle accidents in some cases but not others, and different combinations of data sources and data types may be used to determine the potential injuries for different accidents. As a result, existing systems that rely on a fixed number of data sources from which to receive and analyze accident data, and/or systems that use fixed rule-based techniques, may fail to accurately detect potential injuries.

Therefore, improved techniques are needed for quickly and accurately determining the potential injuries that may result from a vehicle accident, and for initiating specific actions on target computer systems based on the potential injury determinations.

SUMMARY

To address these and other problems and deficiencies in existing technologies, this disclosure describes systems and techniques for training and executing machine learning models configured to determine injury probabilities based on vehicle accident data. In some examples, a training component may construct a machine learning model (e.g., a decision tree model) including various branching criteria based on particular vehicle accident data and ground truth injury data, and leaf nodes storing injury probabilities associated with decision tree branches. A model execution component may execute a trained decision tree model to determine the probability of a potential injury associated with a vehicle accident. Based on the potential injury probability the vehicle accident analysis system may identify one or more target entities and/or target computer systems, and may determine automated processes to initiate on the target systems based on the injury probability.

In various examples, the system may be implemented as an event-driven system, and/or may include cloud-based data storage and services configured to receive, store, and process accident data events. Any number of data sources may operate independently to retrieve and provide accident data to a vehicle accident analysis system. When new or updated accident data is received from a data source, the system may update a vehicle accident store and/or trigger an event to initiate an execution (or re-execution) of a machine learning model to determine (or update) the injury probability associated with the accident. In some cases, the type of accident data received, the data source, and/or the timing of receiving the accident data may determine when and how often the trained model is executed. For instance, the vehicle accident analysis system may include a deduplication component and/or may implement various delay timers in response to receiving updated accident data, thereby control the timing and conditions under which the machine learning model may be executed.

Further, in various examples the vehicle accident analysis system may evaluate and apply injury probability thresholds for routing communications and providing instructions to various target systems. For instance, an injury probability determined for a vehicle accident based on a decision tree model can be compared to any number of probability thresholds associated with various target systems and/or processes that may be invoked on the target systems. The injury probability thresholds associated with the target systems and/or processes can be modified dynamically based on the current workload metrics of each target system, thereby providing a workload control mechanism to allow the analysis system to manage and coordinate the downstream processing of various independent target systems.

In an example of the present disclosure, a computer-implemented method includes receiving, by a computer system and via a first data channel, data associated with a vehicle accident, and generating, by the computer system, a data payload based at least in part on the data associated with the vehicle accident. The method in this example also includes providing, by the computer system, the data payload as input to a machine learning model, and receiving, by the computer system, an output from the machine learning model. Additionally, the method includes determining, by the computer system, an injury probability associated with the vehicle accident, based at least in part on the output from the machine learning model, and determining, by the computer system, a target computer system of an entity associated with the vehicle accident, based at least in part on the injury probability associated with the vehicle accident. The method in this example also includes transmitting, by the computer system, an instruction to the target computer system to initiate a process.

In another example of the present disclosure, a computer system comprises one or more processors, and one or more non-transitory computer-readable media storing computer-executable instructions that, when executed by the one or more processors, cause the one or more processors to perform various operations. The operations in this example include receiving, via a first data channel, data associated with a vehicle accident, retrieving, from an accident data store, previous data associated with the vehicle accident, and generating a payload based at least in part on the data associated with the vehicle accident and the previous data associated with the vehicle accident. The operations in this example further include executing a machine learning model, the executing comprising providing the payload as input to the machine learning model, and determining an injury probability associated with the vehicle accident, based at least in part on an output from the machine learning model. Additionally, the operations in this example include determining a target computer system of an entity associated with the vehicle accident, based at least in part on the injury probability, and transmitting an instruction to the target computer system to initiate a process.

Yet another example of the present disclosure includes one or more non-transitory computer-readable media storing instructions executable by a processor, wherein the instructions, when executed, cause the processor to perform various operations. The operations in this example include receiving, via a first data channel, first data associated with a vehicle accident, receiving, via a second data channel different from the first data channel, second data associated with the vehicle accident, and generating a data payload based at least in part on the first data associated with the vehicle accident and the second data associated with the vehicle accident. The operations in this example further include providing the data payload as input to a machine learning model, receiving an output from the machine learning model, and determining an injury probability associated with the vehicle accident, based at least in part on the output from the machine learning model. Additionally, the operations in this example include determining a target computer system of an entity associated with the vehicle accident, based at least in part on the injury probability, and transmitting an instruction to the target computer system to initiate a process associated with the vehicle accident.

DETAILED DESCRIPTION

Figure 1:
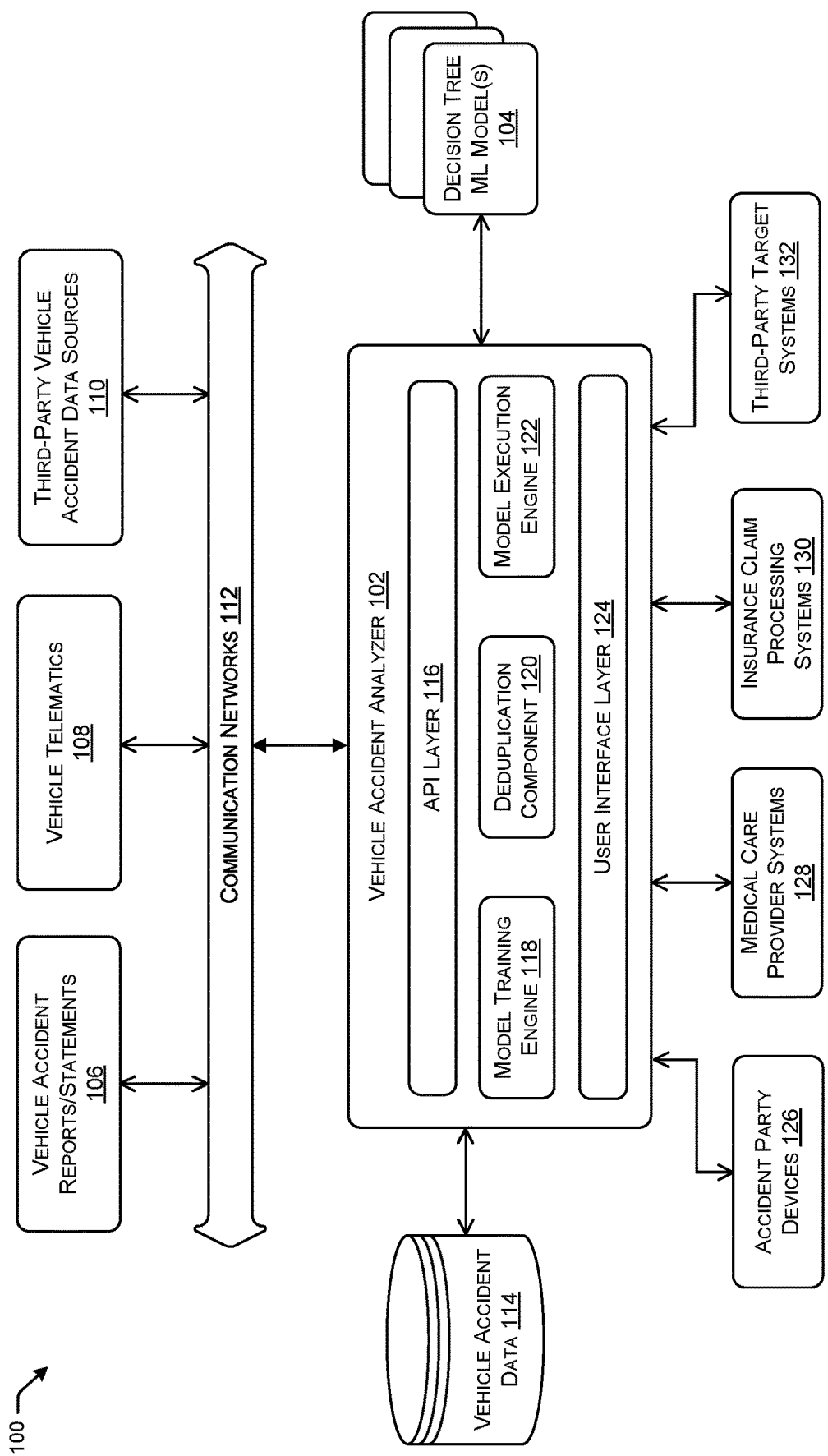
FIG. 1 illustrates an example vehicle accident analysis system including components configured to train and execute machine learning models based on vehicle accident data, and to initiate various processes in target systems based on injury probabilities, in accordance with one or more examples of the present disclosure.

FIG. 1 depicts an example of a computing environment 100 including a vehicle accident analyzer 102 configured to train and execute machine learning (ML) models to detect potential injuries based on vehicle accident data. As shown in this example, the vehicle accident analyzer 102 may train and/or execute ML models 104 (e.g., decision tree ML models) to predict injury probabilities based on vehicle accident data received from various data sources 106-110. The data sources 106-110 may operate separately and independently from one another, to receive and/or determine relevant data associated with a vehicle accident, and may provide the accident data via over one or more data channels (e.g., communication channels, network protocols, and/or communication networks 112) to the vehicle accident analyzer 102. The vehicle accident analyzer 102 may filter and partition the relevant accident data, and then may store the accident data in a vehicle accident data store 114. As described in more detail below; the vehicle accident analyzer 102 may use various combinations of data received from the data sources 106-110 and/or retrieved the data store 114 to train and update ML models 104, as well as to execute the ML models 104 to determine injury probabilities associated with particular vehicle accidents.

As described above, it may be useful for any number of entities, including medical care providers, law enforcement, and/or insurance providers, to receive quick and accurate information regarding the potential injuries incurred during a vehicle accident. However, existing techniques for obtaining injury data associated with vehicle accidents may be costly, time-consuming, and error-prone. For instance, one or more parties to an accident may be unavailable for interviewing, and/or may conceal or fail to report injuries obtained during the accident. Additionally, for certain types of injuries, the injured party might not initially experience symptoms, but might only become aware of the injury in the days or weeks following the accident.

As a result, the trained ML models 104 described herein may provide quicker and more accurate determinations of the likelihood that a vehicle accident may result in potential injuries to the parties involved. ML models 104, which may be implemented as decision tree models in some examples, can receive input data including analyses of the statements from parties or witnesses, vehicle telematics data, analyses of police reports or other accident documents, accident image data, accident location data, weather and traffic data associated with the accident, etc. Based on a payload of relevant input data associated with an accident, the ML models 104 can output data indicating the probability that the accident resulted in one or more injured parties. The vehicle accident analyzer 102 may use injury probability data received from the ML models 104 to determine particular target entities and/or target systems (e.g., medical provider servers, law enforcement servers, insurance provider systems, client devices of parties to the accident, etc.), and may transmit data to and/or initiate processes within selected target systems.

To receive accident-related data from the data sources 106-110, the vehicle accident analyzer 102 may use an application programming interface (API) layer 116, including one or more APIs associated with each of the independent data sources 106-110. In some examples, different ML models 104 may be configured to receive different sets of input data (or payloads). An input payload for an ML model 104 may include any combination of the various input data described herein, including any data received from data sources 106-110 and/or additional data retrieved from a vehicle accident data store 114. After receiving accident data from one or more data sources 106-110, the vehicle accident analyzer 102 may select an ML model 104 to be executed, for example, based on the attributes of the accident such as the state/region of the accident, the time when the accident occurred, the vehicle type, the customer and/or account type, etc. The vehicle accident analyzer 102 may generate a payload of accident-related data compatible with the inputs of the selected ML model 104, and may execute the ML model 104 and provide the payload as input to the ML model 104.

The data sources 106-110 may be implemented as independent computer systems configured to provide specific types and/or ranges of accident-related data to the vehicle accident analyzer 102. Each of the data sources 106-110 may provide one or more particular types of accident data, which may include unique data or may overlap with the data provided by additional data sources. Any of the data sources 106-110 may provide an individual transmission of accident-related data to the vehicle accident analyzer 102, or may provide multiple transmissions of data at different times. The vehicle accident analyzer 102 may receive accident data from the data sources 106-110 according to a predetermined data delivery schedule, or may receive unexpected deliveries of accident-related data from the data sources 106-110 at any time.

In some examples, the vehicle accident analyzer 102 may include an event-driven system, in which the vehicle accident analyzer 102 subscribes to receive accident data "events" (e.g., transmissions of new or updated accident-related data) from each of the data sources 106-110. When an accident data event is received, the vehicle accident analyzer 102 may store the updated accident data in the vehicle accident data store, and may trigger the execution of the appropriate ML model(s) 104 to determine updated injury probabilities for the accident. In such examples, any or all of the components of the event-driven system, including the data sources 106-110, vehicle accident analyzer 102, vehicle accident data store 114, event queues, buffers, etc., may be cloud-based components implemented within a public cloud, private cloud, and/or hybrid cloud environment. Additionally or alternatively, any or all of these components may be implemented in on-premise data centers or servers, or in other non-cloud computing environments.

Although FIG. 1 depicts only three examples of data sources 106-110, it can be understood from the context of this disclosure that any number of independent data sources may be used to provide various accident-related data to the vehicle accident analyzer 102. In this example, the data source 106 may represent one or more data sources providing reports and/or statements from the parties or witnesses to a vehicle accident. For example, the data source(s) 106 may be associated with medical providers, first responders, insurance representatives, etc., and may provide transcripts of written or recorded statements made by the parties involved or witnesses to an accident. The reports or statements provided by the data source(s) 106 also may include image data and/or video recordings of the individuals providing the statements. In some cases, instead of (or in addition to) transcripts or recordings, the data source 106 may provide second-hand statements such as the notes taken by an interviewer or examiner (e.g., an emergency medical technician, nurse, doctor, police officer, insurance agent or representative, etc.) during a discussion with the party or witness to the accident. As described below; the vehicle accident analyzer 102 may receive reports and/or statements associated with an accident from data source(s) 106, and may analyze and extract data from the reports and/or statements, including accident-related keywords, tone or emotion indicator data, user verification data, background noise, and the like. Based on the analysis and/or data extracted from these reports and statements, the vehicle accident analyzer 102 may determine input data for the ML models 104.

In this example, the data source 108 may represent one or more vehicle telematics data sources providing internal system data from one or more vehicles involved in an accident. For example, a telematics data source 108 may provide the vehicle accident analyzer 102 with a set of internal state data from a vehicle, during a time range associated with the accident. A vehicle telematics system, for instance, may detect that an accident has occurred and may store the time and location (e.g., GPS coordinates and/or street data) associated with the accident, as well as additional vehicle state data corresponding to time and location of the accident. The vehicle state data provided by a data source 108 may include, for example, the vehicle speed, steering angle, lateral and/or longitudinal acceleration, impact location on the vehicle, and/or the control commands (e.g., steering, braking, acceleration, horn, lights, signals, etc.) performed by the vehicle before, during, and after the accident. Vehicle state data also may include the number of passengers at the time of the accident, the types of passengers (e.g., adults or children, etc.), and/or where in the vehicle each passenger was sitting. As described below, the vehicle accident analyzer 102 may receive any combination of telematics data from vehicle telematics data source(s) 108, for a single vehicle or multiple vehicles involved in an accident, and may use the telematics to determine input data for the ML models 104.

In this example, the data source 110 may represent one or more third-party data sources providing additional relevant data associated with a vehicle accident. For instance, data source(s) 110 may include public or private data sources providing weather data, traffic data, visibility data, road surface data, road conditions data, and the like, associated with a vehicle accident. Additional data source(s) 110 may include data identifying an exact time and/or location of the accident (e.g., a particular road, lane, shoulder, etc.). Data source(s) 110 also may include third-party data sources providing image or video data associated with the accident (e.g., traffic cameras, security cameras, dashboard camera videos from nearby vehicles, mobile device pictures or videos captured by witnesses, etc.). As described below, the vehicle accident analyzer 102 may receive any combination of the data received from third-party data source(s) 110, and may use the data to determine input data for the ML models 104.

In various examples, any of the data sources 106-110 may provide data to the vehicle accident analyzer 102 in response to requests (e.g., a web-based request or web services request) from the vehicle accident analyzer 102, or proactively using an event-driven architecture in which the vehicle accident analyzer 102 subscribes to receive particular types of data events from the data sources 106-110. When the vehicle accident analyzer 102 receives data from the data sources 106-110, it may determine a vehicle accident associated with the data (e.g., based on a vehicle identifier, party/witness name, time, location, etc.) and store the data within the vehicle accident data store 114. As described below, the vehicle accident analyzer 102 may use a combination of new/updated data received from the data sources 106-110 and previous data stored in the vehicle accident data store 114, to generate a data payload that can be used as input to an ML model 104. Therefore, the vehicle accident analyzer 102 may execute and re-execute an ML model 104 multiple times as new/updated data is received via the data source(s) 106-110, to determine updated injury probabilities for an accident based on the new/updated data.

Using a combination of accident-related data received from the data sources 106-110 and data stored in the vehicle accident data store 114, the vehicle accident analyzer 102 may train and execute ML models 104 to determine the injury probabilities associated with particular vehicle accidents. As described below in more detail, the vehicle accident analyzer 102 may include a model training engine 118 to train and update ML models 104, a deduplication component 120 to determine and implement delay timers that to control the timing and conditions for executing the ML models 104, and a model execution engine 122 to generate data payloads associated with particular accidents and execute the ML models 104 based on the data payloads.

After executing the ML model(s) 104 to determine an injury probability associated with an accident, the vehicle accident analyzer 102 may use the injury probability to determine various downstream processes to initiate and/or the various target entities and systems on which the downstream processes are to be initiated. For instance, based on the injury probability output by an ML model 104 for a particular vehicle accident, the vehicle accident analyzer 102 may select one or more particular target systems 126-132, and particular instructions/data to be transmitted to the selected target systems 126-132 to initiate processing tasks associated with the accident on the target systems. The outputs from the vehicle accident analyzer 102 to the target systems 126-132 may take the form of the notifications, messages, web service invocations, API calls, and the like, any or all of which may cause processing tasks to be executed in the selected target system 126-132. In some examples, the vehicle accident analyzer 102 also may provide a user interface layer 124 included various target-specific user interfaces to allow users of the target devices to view and/or update various accident data, payload data, configure or re-execute the ML models 104, etc.

Although FIG. 1 includes four examples of target systems 126-132 that may be accessed and controlled by the vehicle accident analyzer 102 in response to the execution of the ML models 104, it can be understood from the context of this disclosure that any number of additional target systems may be used in other examples. In this example, the target system 126 may represent one or more client devices associated with the parties involved in the vehicle accident. Target system(s) 126 may include, for example, desktop or laptop computers, tablet computers, smartphones and/or other mobile devices (e.g., wearable devices, etc.). Based on the injury probabilities determined for an accident, the vehicle accident analyzer 102 may initiate a message (e.g., notification and/or user interface) on a target system 126. Messages to target systems 126 can include requests to a party or other individual for additional input data to be used by the ML models 104. Additional messages to target systems can invoke notifications or user interfaces including instructions for the party/individual to seek medical care, complete electronic forms relating to law enforcement, insurance claim processing, etc.

In this example, the target system 128 may represent one or more medical care provider systems associated with the parties involved in the accident. Target system(s) 128 may include, for example, medical provider servers, web portals, etc., to allow the vehicle accident analyzer 102 to initiate medical care requests and/or upload accident-related information directly to a medical care provider system. For instance, based on the injury probabilities determined for an accident, the vehicle accident analyzer 102 may initiate a medical examination request for a party involved in the accident, and/or may provide (e.g., via a secure upload) any relevant accident data from the vehicle accident data store 114 and/or data sources 106-110 to the target systems 128.

In this example, the target system 130 may represent one or more insurance provider systems associated with the parties involved in the accident. Target system(s) 130 may include, for example, insurance servers, insurance agent systems, web portals for entry of insurance-related data, etc. Based on the injury probabilities determined for an accident, the vehicle accident analyzer 102 may open and/or modify insurance claims automatically via the target systems 130, may route claims internally within the insurance provider to specific claim-handling groups or representatives, etc. The vehicle accident analyzer 102 also may provide (e.g., via a secure upload) any relevant accident data from the vehicle accident data store 114 and/or data sources 106-110 to the target system(s) 130.

In this example, the target system 132 may represent one or more third-party systems associated with the vehicle accident. Target system(s) 132 may include, for example, law enforcement servers, client devices of witnesses, claimants, and/or vehicle repair facilities, and/or other third-party entities associated with the accident. Based on the injury probabilities determined for an accident, the vehicle accident analyzer 102 may transmit potential injury data, party data, and/or any other accident-related data, to the various target system(s) 132.

In various examples, the vehicle accident analyzer 102 may determine and implement injury probability thresholds for any or all of the target systems 126-132. For instance, after using an ML model 104 to determine an injury probability associated with an accident, the vehicle accident analyzer 102 may compare the injury probability to one or more probability thresholds associated with each of the target systems 126-132. Based on the comparison of the injury probability of the accident to the probability thresholds of the target systems 126-132, the vehicle accident analyzer 102 may determine which target systems are to be contacted and/or which processes are to be invoked on the target systems. As an example, if a first execution of an ML model 104 based on accident-related data outputs a first injury probability below a probability threshold for initiating a medical exam, then the vehicle accident analyzer 102 may determine that the medical provider target system 128 is not to be contacted to request to the medical exam. However, after receiving additional accident-related data from one or more data sources 106-110, the vehicle accident analyzer 102 may re-execute the ML model 104 based on the updated data. In this example, if the re-execution of the ML model 104 outputs a second injury probability above the probability threshold for initiating a medical exam, then the vehicle accident analyzer 102 may transmit instructions to the medical provider target system 128 to request to the medical exam.

As noted above, various injury probability thresholds may be determined by the vehicle accident analyzer 102 for particular target systems and/or particular processes to initiate on the target systems. For instance, a first injury probability for an accident may cause a first process to be initiated on an insurance claim processing target system 130, and a second different injury probability may cause a second process to be initiated on the same target system 130. The vehicle accident analyzer 102 also may modify the probability thresholds associated with the target systems and/or the target processes to be invoked. For instance, based on the current workload of a particular target system (e.g., in terms of computing resources, memory, available personnel, etc.), the vehicle accident analyzer 102 may raise or lower the injury probability thresholds associated with the target system. By adjusting the probability thresholds for the target system, the vehicle accident analyzer 102 may cause more or less accident-related processing tasks to be invoked on the target system, thereby providing a control mechanism for managing and coordinating the downstream processing workload across the target systems 126-132, and for prioritizing the most valuable accident-related processing tasks (e.g., corresponding to the greatest probability of injuries) over less valuable processing tasks.

When an accident involves multiple vehicles, a single ML model 104 may be trained to output an injury probability for the accident as a whole. In other examples, the vehicle accident analyzer 102 may train and use separate ML models 104 (or may re-execute the same ML model 104 with different input data) to determine the separate injury probabilities associated with each of the vehicles involved in the accident. Additionally, for multi-vehicle accidents, vehicle accident analyzer 102 may invoke different combinations of target systems 126-132 and/or different processes depending on the injury probabilities associated with the different vehicles. As an example, if the ML model(s) 104 executed for a multi-vehicle accident indicate a relatively high injury probability associated with a first vehicle and a relatively low injury probability associated with a second vehicle, then the vehicle accident analyzer 102 may invoke one set of processes on particular target systems 126-132. However, in this example, if the ML model(s) 104 indicated a relatively low injury probability for the first vehicle and a relatively high injury probability for the second vehicle, then the vehicle accident analyzer 102 may invoke a different set of processes on a different set of target systems 126-132. Additionally, the injury probability thresholds determined and stored by the vehicle accident analyzer 102 for the target systems 126-132 and/or target processes to be invoked, also may include separate probability thresholds associated with different vehicles in a multi-vehicle accident and/or individual passengers within each vehicle.

As illustrated by the examples above, the system depicted in FIG. 1 may provide technical advantages in operating vehicle accident analysis systems, and more generally in training and executing machine learning models in event-based computing infrastructures. For example, the vehicle accident analyzer 102 can train and execute machine learning models to quickly and accurately identify potentially injured parties based on vehicle accident data. The vehicle accident analyzer 102 can use various machine learning models to determine more accurate probability predictions for accident injuries, based on payloads that include combined data from various data sources. As a result, the vehicle accident analyzer 102 may improve overall vehicle safety and individual health outcomes when vehicle accidents occur, through early and accurate detection of potential injuries, even when those injuries may be unreported, concealed, and/or unknown to the other parties involved in the accident.

Figure 2:
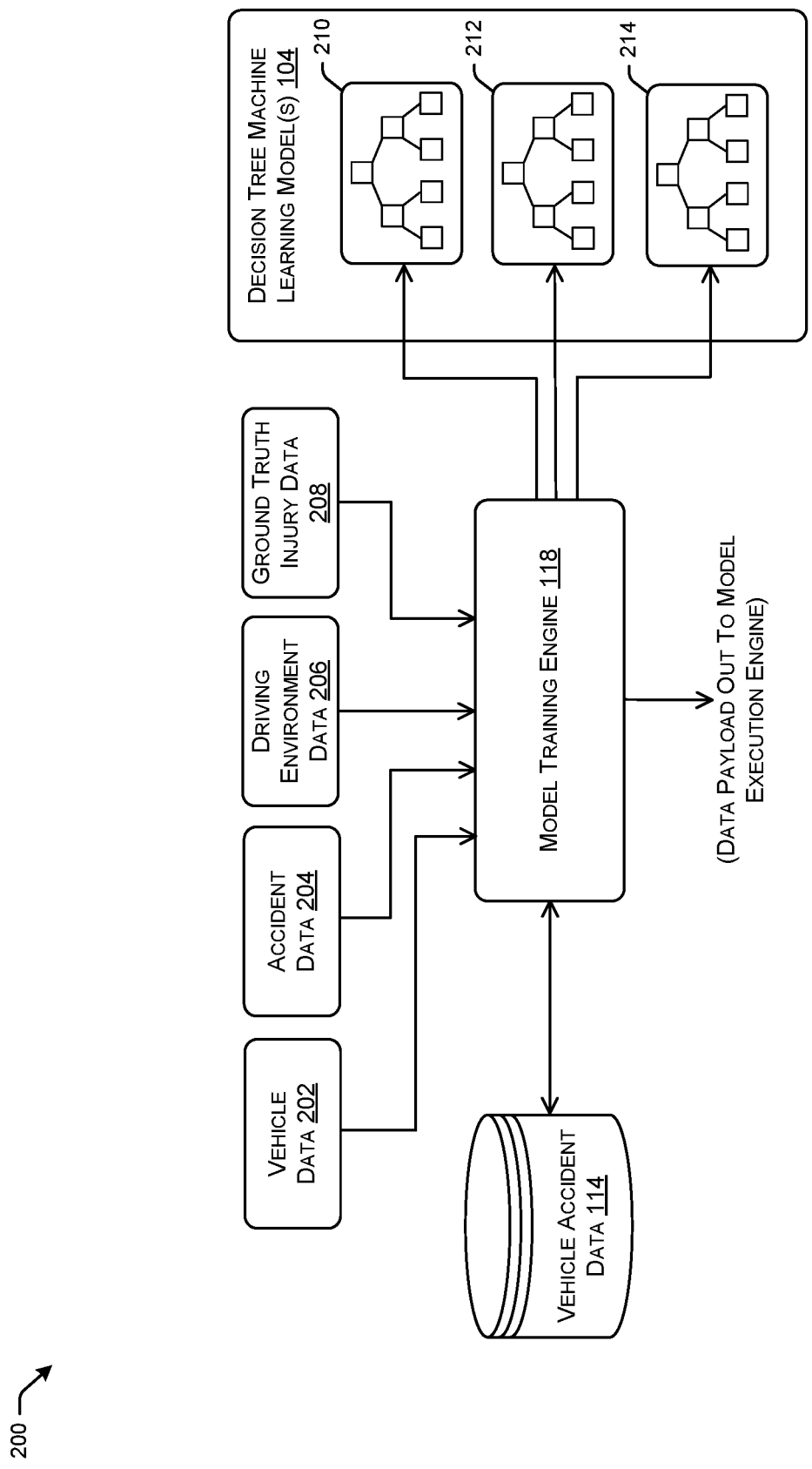
FIG. 2 illustrates another example vehicle accident analysis system configured to train decision tree machine learning models based on vehicle accident data, ground truth injury data, and/or other data sources, in accordance with one or more examples of the present disclosure.

FIG. 2 depicts another example computing environment 200 including a model training engine 118 configured to construct and train ML models 104 based on various vehicle data, accident data, and/or ground truth injury data. In some examples, the computing environment 200 may use similar or identical components to those in computing environment 100 discussed above, in which the same (or a similar) model training engine 118 may be implemented within a vehicle accident analyzer 102. In other examples, the computing environment 200 may be different from the computing environment 100, and the model training engine 118 and model execution engine 122 may be implemented in separate computing systems/environments. For instance, the model training engine 118 and/or vehicle accident data store may be implemented within a cloud-based computing environment, while the model execution engine 122 may operate in an on-premise data center associated with the vehicle accident analyzer 102.

The model training engine 118 may generate and train ML models 104 based on various sources of vehicle accident-related data, including vehicle data 202, accident data 204, driving environment data 206, and/or ground truth injury data sources 208. As noted above, various vehicle-related and/or accident-related data may be received from various external data sources, or may be retrieved from the vehicle accident data store 114. In this example, vehicle data 202 may include attributes associated with a vehicle involved in an accident, such as the make, model, year, trim, and/or additional features of the vehicle. Accident data 204 may include any of the accident-related data described above in reference to FIG. 1, including (but not limited to) any of the data received from the data sources 106-110. Driving environment data 206 may, for example, weather data, traffic data, visibility data, road surface data, and/or image/video data associated with an accident. Finally, ground truth injury data may include records from medical providers, law enforcement data, insurance reports, etc., identifying injuries to individuals involved in vehicle accidents. For a previous vehicle accident (or any number of previous vehicle accidents), the combination of data 202-208 associated with the previous accident(s) may be received by the model training engine 118, and used to train one or more ML models 104 to output injury probabilities associated with accidents.

As shown in this example, the ML models 104 trained by the model training engine 118 may include decision tree ML models. A decision tree ML model 104 may comprise a tree structure having accident-related branching criteria associated with each branching point in the structure, and a distinct injury probability associated with each leaf node in the structure. In various examples, any number of different variants of decision tree algorithms may be used to implement the ML model 104, including but not limited to Iterative Dichotomiser 3 (ID3), Classification And Regression Tree (CART), Chi-square automatic interaction detection (CHAID), multivariate adaptive regression splines (MARS), and/or Conditional Inference Trees. It can also be understood from the context of this disclosure that in other examples the model training engine 118 may implement ML models 104 using various additional or alternative machine learning techniques and algorithms. For instance, the ML models 104 may include artificial neural network data structures having one or more levels, different node configurations, randomly assigned initial node weights, and the model training engine 118 may use one or more regression algorithms, instance-based algorithms, Bayesian algorithms, clustering algorithms artificial neural network algorithms, and/or deep learning algorithms, to train the ML models 104. Different ML models 104 also may implement different machine-learning algorithms including, but not limited to, regression algorithms instance-based algorithms, Bayesian algorithms, clustering algorithms, association rule learning algorithms, deep learning algorithms supervised learning, unsupervised learning, semi-supervised learning, etc.

The model training engine 118 may generate and train a single ML model 104 to determine injury probabilities based on accident input data, or may generate and train multiple ML models 104 corresponding to different training data sets. As shown in this example, the model training engine 118 has generated a number of different ML models 104, including ML model 210, ML model 212, and ML model 214. In this example, the different ML models 210-214 may be based on different sets of training data corresponding to different time periods, different vehicle types, different driving regions, different weather conditions, different driving scenarios, and/or different accident types, etc. In such examples, the model training engine 118 may generate and train multiple ML models 104 to apply to different accident scenarios or attributes, and the model execution engine 122 may select and execute an appropriate ML model 104 based on the characteristics of the accident.

As described below in more detail, each ML model 104 may have an associated set of input data (or payload) determined by the model training engine 118. For instance, during the training process for a decision tree model 104 (or other ML model type), the machine learning algorithms of the model training engine 118 may determine which accident-related data is relevant (e.g., outcome determinative) to predicting potential injuries associated with the accident. The relevant accident-related data may be identified and used to determine the branching criteria for the decision tree ML model 104 (or input data for other ML model types, etc.). Other accident-related data may be determined by the model training engine 118 to be irrelevant (or less relevant) as a predictor of potential injuries from an accident, and this irrelevant (or less relevant) data may be excluded as input data from the ML model 104.

A data payload (or payload) may refer to the set of relevant accident data provided as input to an ML model 104 configured to output injury probability data associated with the accident. It can be understood that different ML models 104 may use different combinations of accident-related data as input, and thus may have different payloads. In some examples, the model execution engine 122 may determine which ML model 104 to execute for an accident, by comparing the different payloads of the ML models 104 to the set of data that is currently available for an accident. For instance, when an initial set of accident-related data is received shortly after an accident has occurred, the model execution engine 122 may select and run a first ML model 104 for which the initial accident data set satisfies the data payload. In examples in which additional accident-related data is received for the same accident (e.g., at a later time), the model execution engine 122 may select and run a second and more robust ML model 104 having a larger payload and greater performance in predicting potential injuries.

Figure 3:
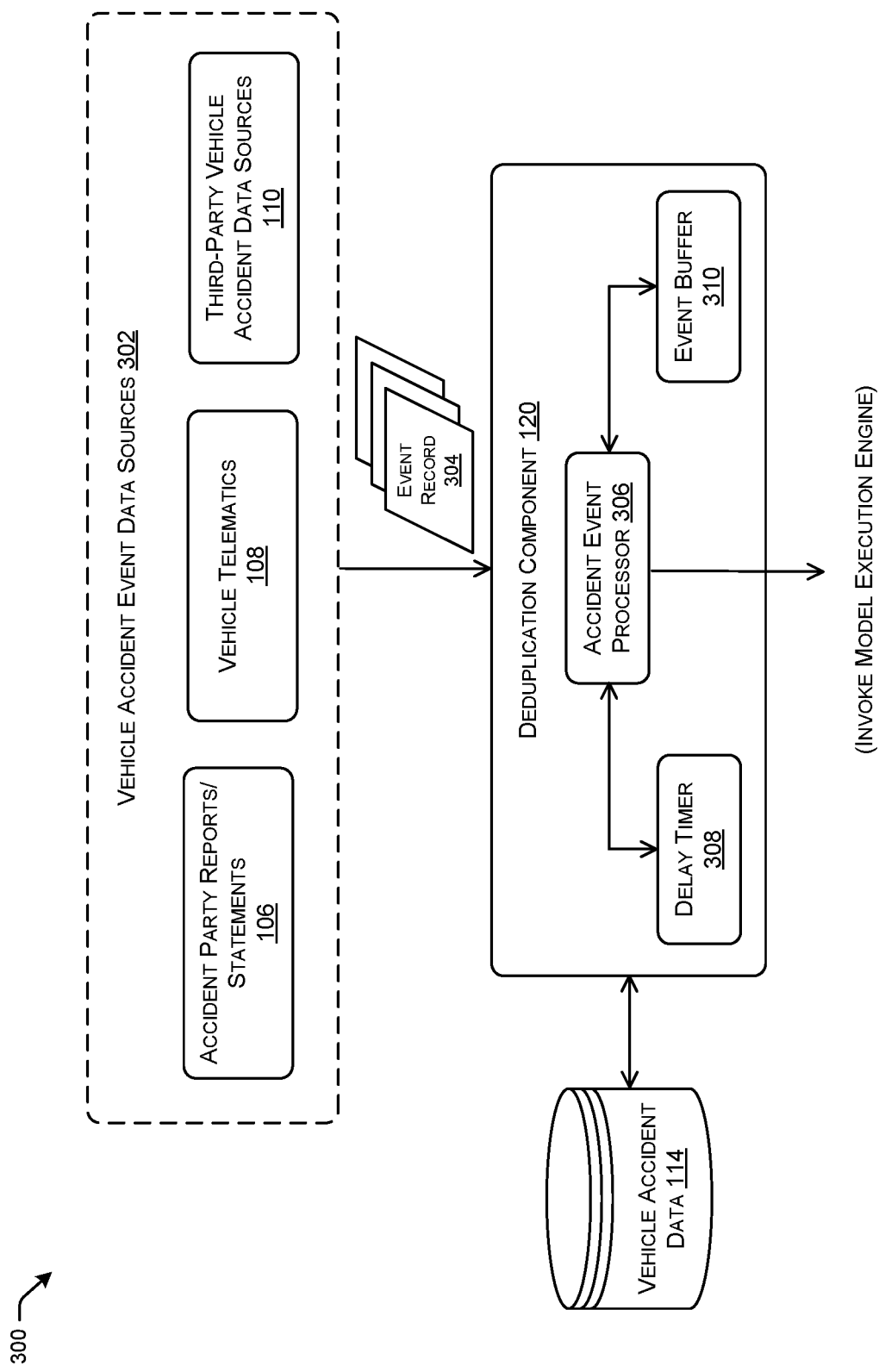
FIG. 3 illustrates another example vehicle accident analysis system configured to receive data events associated with a vehicle accident, and execute a train decision tree machine learning model to determine an injury probability associated with the vehicle accident, in accordance with one or more examples of the present disclosure.

FIG. 3 depicts another example computing environment 300 including a deduplication component 120 (which may be similar or identical to the deduplication component 120 depicted in FIG. 1) configured to control the timing and frequency of executions of the ML models 104. As described below; the deduplication component 120 may implement delay timers and/or event buffers based on updated accident data from the data sources 106, to control the timing and conditions under which the ML models 104 may be executed. Accordingly, the deduplication component 120 can be configured to save computational resources and improve the efficiency of the vehicle accident analyzer 102, by optimally determining when and how often ML models 104 are executed in response to receiving updated accident data.

As shown in this example, the deduplication component 120 can be used within event-driven systems and architectures. However, a deduplication component 120 may be used similarly or identically in other types of systems as well (e.g., non-event systems). In an event-driven system, the vehicle accident analyzer 102 may subscribe to and receive new or updated accident-related data as data events. Data events including new or updated accident data can be provided by any number of data sources 302, such as data sources 106-110 (which may be the same or similar as the data sources 106-110 depicted in FIG. 1). As noted above, although some accident data may be available shortly after an accident has occurred, other accident data such as party or witness statements, police reports, medical reports, driving conditions data, vehicle telematics data, and the like, might not be immediately available after an accident. Instead, this delayed accident data may be received via the independent data sources 106-110, at unpredictable and/or inconsistent times that may range between a few minutes and several months after an accident has occurred.

In some event-driven systems, a vehicle accident analyzer 102 may be configured to re-execute one or more ML models 104 in response to receiving new or updated accident-related data from the data sources 106-110. Although re-executing the ML model(s) 104 in response to receiving updated accident data may improve the accuracy of the determined injury probabilities, excessive re-execution of the ML model(s) 104 may use significant computing resources and reduce the efficiency and workload capabilities of the vehicle accident analyzer 102. As an example, within a single statement from a party or witness to an accident, or a single batch of telematics data, many different accident data fields may be updated in the vehicle accident data store 114. In this example, the vehicle accident analyzer 102 were to re-execute an ML model 104 each time a data field is updated, the number of re-executions may be unnecessarily excessive, and the hardware and software resources of the vehicle accident analyzer 102 may be quickly depleted causing system errors and failures.

To address these problems, the deduplication component 120 may prevent the vehicle accident analyzer 102 from re-executing the ML model(s) 104 after each accident-related data event. As shown in this example, when the vehicle accident analyzer 102 receives an event record 304 from an accident-related data source 302, the deduplication component 120 may analyze the event with an accident event processor component 306. The accident event processor component 306 may use the type of data received in the event record 304, the data source 302 from which the event record 304 was received, and/or the relative timing of the event record 304 compared to other received event records, to determine whether or not to execute an ML model 104 based on the received event record 304.

In some cases, based on the type and amount of accident data received, the data source 302 providing the data, and/or the timing of the data, the accident event processor component 306 may immediately invoke the model execution engine 122 to execute (or re-execute) the ML model(s) 104 to update the injury probability for the accident. In other cases, the accident event processor component 306 may determine that the ML model(s) 104 should not be executed immediately in response to the event record 304. For instance, the accident event processor component 306 may determine that the data in the event record 304 is unlikely to significantly change the injury probability output by the ML model(s) 104 for the accident. Additionally or alternatively, the accident event processor component 306 may determine that there is a likelihood that additional accident-related data will be received in the near future. In these instances, the accident event processor component 306 may instantiate a delay timer 308 and/or may store the event record temporarily in an event buffer 310. During the duration of the delay timer 308 (e.g., 5 seconds, 10 seconds, 15 seconds, etc.), any additional event records 304 received by the vehicle accident analyzer 102 may be stored in the event buffer 310. When the delay timer 308 completes, the accident event processor component 306 may store any new or updated accident data from the event buffer 310 into the vehicle accident data store 114, clear the event buffer 310, and invoke the model execution engine 122 to execute (or re-execute) the ML model(s) 104 to update the accident injury probability based on the new or updated data records.

Figure 4:
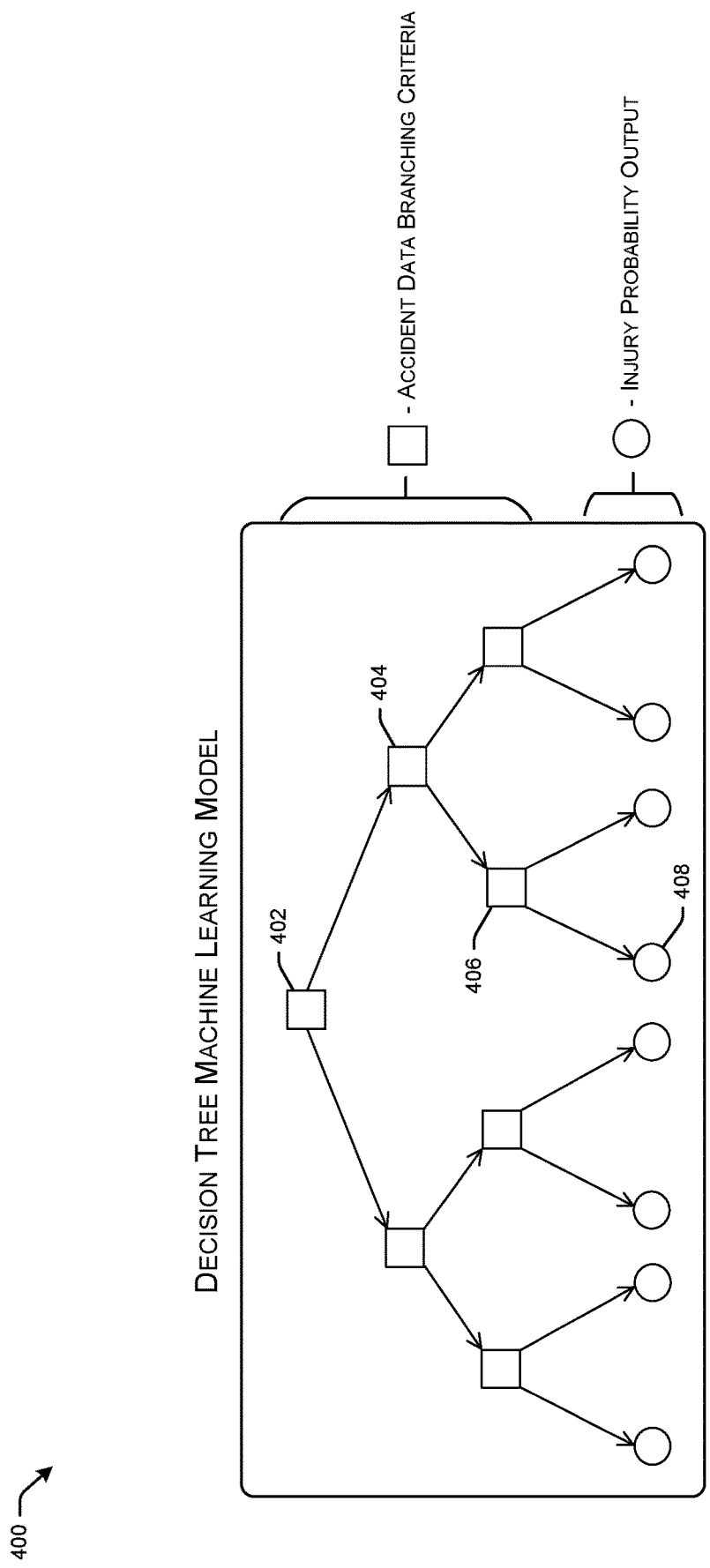
FIG. 4 illustrates an example decision tree model, including branching criteria based on vehicle accident data and output nodes corresponding injury probability data, in accordance with one or more examples of the present disclosure.

FIG. 4 shows an example decision tree model 400, including branching criteria based on vehicle accident data and output nodes corresponding injury probability data, in accordance with one or more examples of the present disclosure. In some examples, any or all of the ML models 104 described herein may be implemented as a decision tree model 400. In such examples, decision tree ML models may provide particular efficiency advantages when evaluating accident data to determine injury probabilities. However, in other examples, the ML models 104 may be implemented using artificial neural network structures or any other type of machine learning models and/or algorithms.

As shown in this example, the decision tree model 400 may include a tree data structure including a number of branching nodes having associated branching criteria, and leaf nodes storing associated injury probability data. Each of the branching criteria in this example may be based on or more of the accident-related data described herein, and may provide a binary (or non-binary) threshold for determining which branch to follow while evaluating the accident data. For instance, in this example, the first branching node 402 may represent a branching criteria based on which party provided the accident data (e.g., the party associated with the data channel over which the accident data was received). The second branching node 404 may represent a branching criteria based on the time the accident was reported relative to the time that the accident occurred. The third branching node 406 may represent a branching criteria based on the presence or absence of a particular keyword in the accident description provided by a party to the accident. Examples of keywords that can be used as branching criteria within a decision tree model 400 may include, for instance, keywords (or phrases) such as "rolled over," "sliding." "head-on," "broken glass," etc. Finally, in this example, the leaf node 408 may store one possible output of the model (e.g., an injury probability) associated with the particular branch of the decision tree defined by the particular branching criteria at branching nodes 402-408. Although the example decision tree model 400 shown in FIG. 4 depicts a simple model using binary branching and a relatively small number of nodes and levels, it can be understood that any number and configuration of tree branches, accident-related branching criteria, and/or injury probability outputs may be used in other examples.

Figure 5:
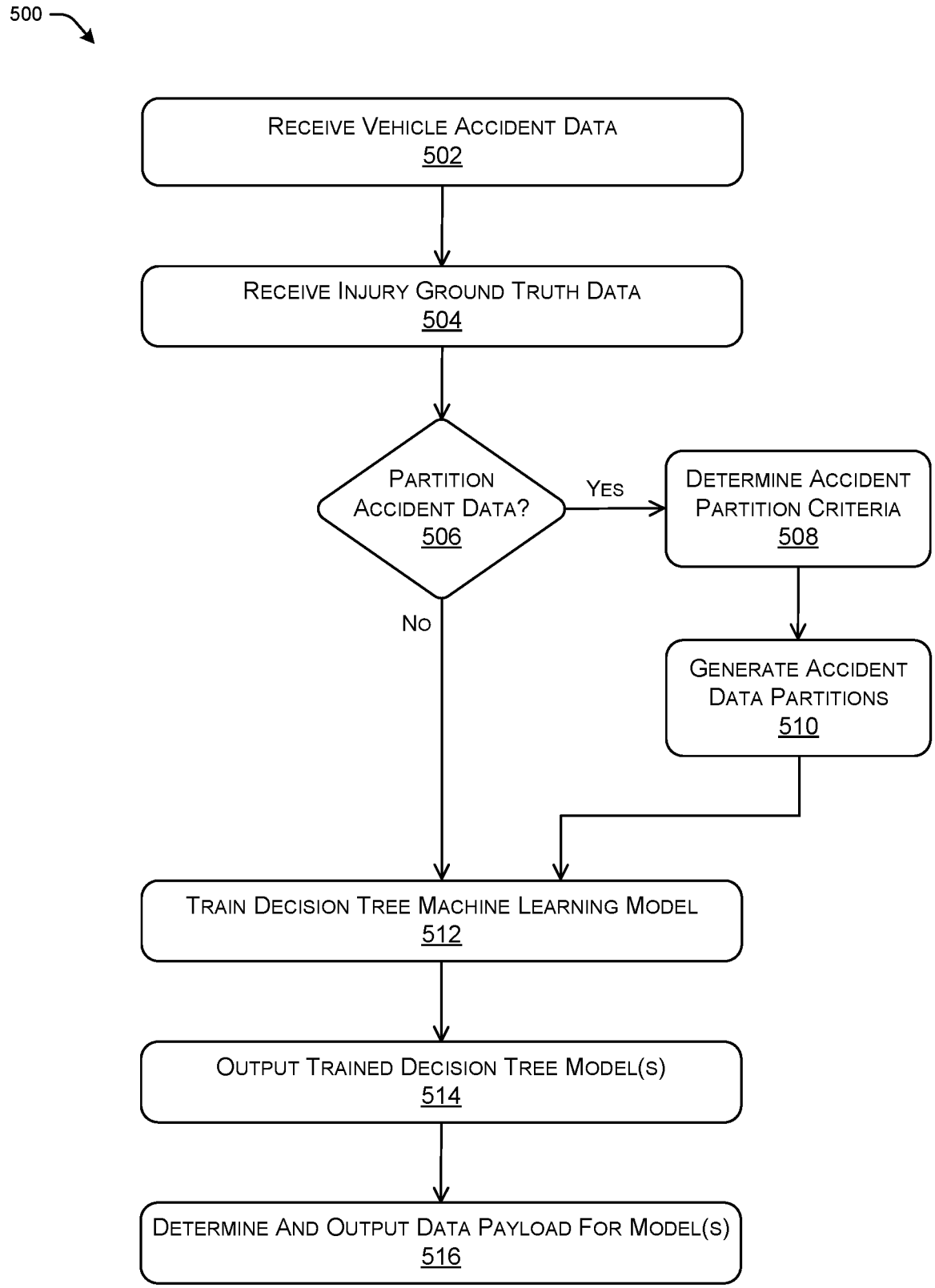
FIG. 5 illustrates an example process of training machine learning models to output injury probability data based on vehicle accident data from various data sources, in accordance with one or more examples of the present disclosure.

FIG. 5 is a flow diagram illustrating an example process 500 of training a machine learning model to output an injury probability associated with a vehicle accident, based on accident-related data from various data sources. In various examples, some or all of the operations of process 500 may be performed by a model training engine 118 associated with a vehicle accident analyzer 102. As described below; the model training engine 118 may use combinations of associated accident-related data and ground truth injury data to train one or more ML models 104 to determine injury probabilities associated with vehicle accidents. A model training engine 118 may be implemented within a vehicle accident analyzer 102, as depicted in FIG. 1, or may be implemented within a separate server and/or computing environment. In various examples, the model training engine 118, and/or the data sources from which the training data is received, may be implemented in a public, private, or hybrid cloud in a cloud computing environment, or may be implemented in an on-premise data center.

At operation 502, the model training engine 118 may receive historical accident data associated with one or more previous vehicle accidents. In some examples, the model training engine 118 may receive the historical accident data from one or more of the data sources 106-110, and/or from the vehicle accident data store 114. Examples of the historical accident data may include statements, reports, and/or other information provided by the parties or witnesses to an accident. Additional examples of historical accident data may include data reports or statements from medical providers, first responders, insurance representatives, etc., and may include transcripts of written or recorded statements made by the parties involved or witnesses to an accident. Further examples of historical accident data may include the vehicle specifications, vehicle telematics data, image or video data associated with the accident, and/or the driving conditions associated with the accident.

At operation 504, the model training engine 118 may receive ground truth injury data associated with the same set of previous accidents for which data was received in operation 502. As discussed above, ground truth injury data associated with previous accidents may include records from medical providers, law enforcement data, insurance reports, and the like. The ground truth injury data may include data identifying documented injuries to individuals involved in the previous accidents.

At operation 506, the model training engine 118 may determine whether the historical accident data and ground truth data, received in operations 502 and 504 respectively, are to be partitioned into multiple training data sets. In some examples, the model training engine 118 may use a single training data set to train a single ML model 104 for determining injury probabilities based on any payload of accident-related data. In such examples, the model training engine 118 may determine not to partition the historical accident data and ground truth data into multiple data sets (506: No).

In other examples, the model training engine 118 may use multiple different sets of training data and may train multiple ML models 104. In these examples, each of the ML models 104 can be associated with one or more classifications of vehicles, accidents, or injuries, etc. For instance, a first ML model 104 can be executed for accidents involving a particular vehicle type, and a different ML model 104 can be executed for accidents involving a different vehicle type. As another example, a first ML model 104 can be executed for accidents occurring in a particular state/region and in particular weather conditions, while different ML models 104 can be executed for accidents occurring in different states/regions and in different weather conditions, etc. In these examples, the model training engine 118 may determine that the historical accident data and ground truth data are to be partitioned into multiple data sets (506: Yes). Accordingly, at operation 508, the model training engine 118 may determine one or more criteria for partitioning the historical accident and injury data. Examples of criteria may include any combination of vehicle data, accident-related data (e.g., party or witness statement data, telematics data, driving condition data, etc.) and/or injury data. Then, at operation 510, the model training engine 118 may generate the accident data partitions and partition the data into multiple separate training data sets, each of which may be used to train a separate ML model 104.

At operation 512, the model training engine 118 may train one or more ML models 104 based on the training data sets determined in operations 506 and/or 510. In some examples, the model training engine 118 may construct and train decision tree ML models comprising tree structures with accident-related branching criteria, and injury probabilities associated with each leaf node. However, in other examples, the model training engine 118 may implement ML models 104 using various other machine learning techniques and algorithms, including (but not limited to) neural network-based ML models. The ML models 104 generated and trained by the model training engine 118 may implement various different machine-learning algorithms, such as regression algorithms instance-based algorithms, decision tree algorithms, Bayesian algorithms, clustering algorithms, association rule learning algorithms, deep learning algorithms supervised learning, unsupervised learning, semi-supervised learning, etc.

At operation 514, the model training engine 118 may output and/or store the decision tree model(s) generated and trained in operation 512. The decision tree model(s) may be stored as ML models 104 in a server (or other computer storage) associated with the vehicle accident analyzer 102. In some cases, model training engine 118 may operate in one computing environment (e.g., a cloud-based environment) to receive accident-related data and train the models, and may provide the trained models to a vehicle accident analyzer 102 computer system operating in a separate computing environment (e.g., an on-premise datacenter) for execution.

At operation 516, the model training engine 118 may determine payload information associated with the trained ML model(s) 104, and may output the payload information to one or more systems associated with a model execution engine 122. As noted above, a data payload may include a set of accident-related data provided as input to the ML models 104. Different ML models 104 may have different payload data corresponding to different combinations of accident-related input data. In some examples, the model training engine 118 may provide payload information for each ML model 104 to the model execution engine 122, which may use the payload information to determine which ML model(s) 104 to execute based on the available accident data.

Figure 6:
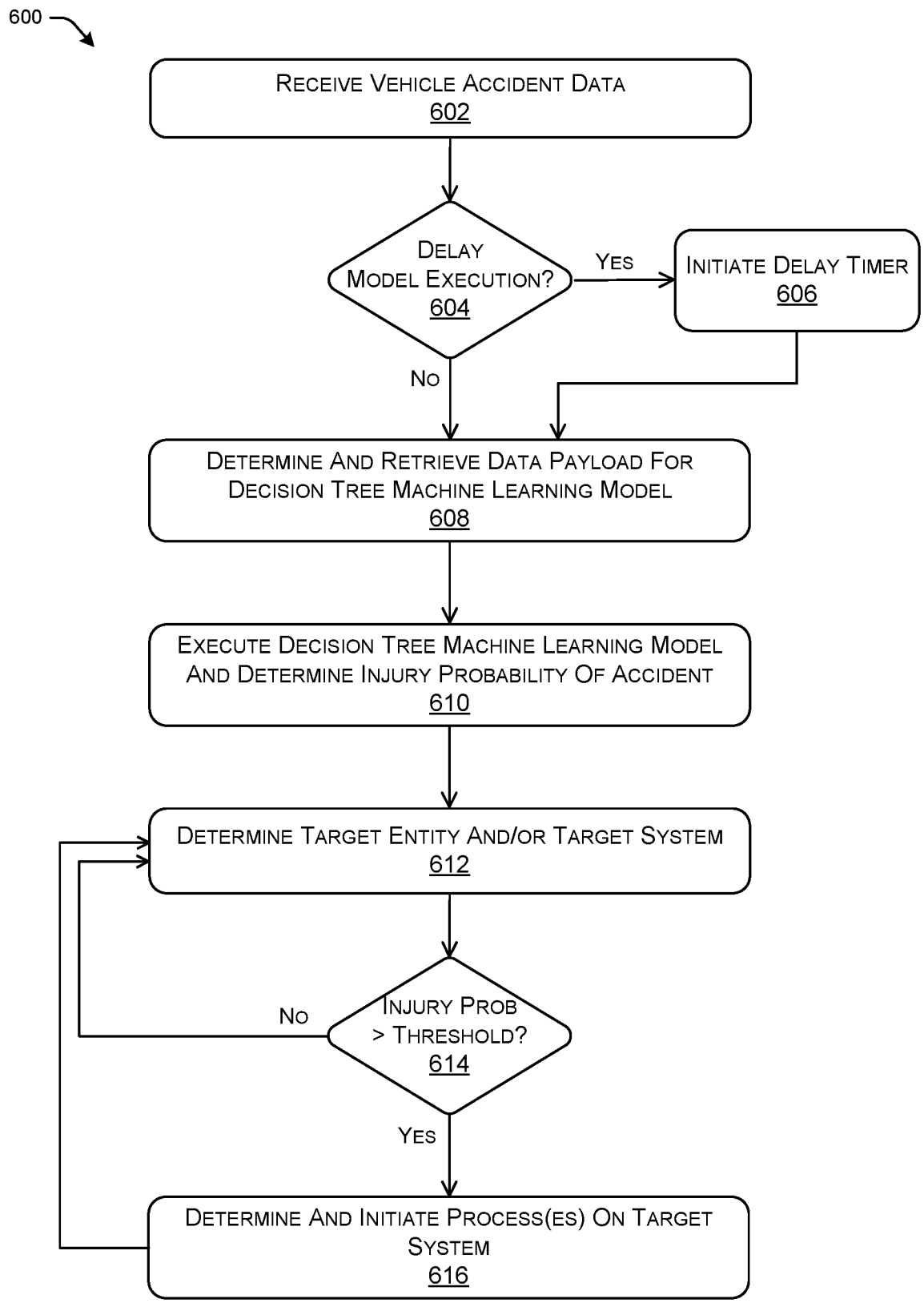
FIG. 6 illustrates an example process of executing a machine learning model based on vehicle accident data, and determining and initiating processes on target systems based on the model output, in accordance with one or more examples of the present disclosure.

FIG. 6 is a flow diagram illustrating a process 600 of selecting and executing a trained ML model 104 configured to output an injury probability based on vehicle accident data, and using the model output to determine and initiate processes on one or more target systems. In various examples, some or all of the operations of process 600 may be performed by a vehicle accident analyzer 102 including a model execution engine 122 and/or a deduplication component 120. As described below, one or both of the vehicle accident analyzer 102 and the model execution engine 122 may be implemented within a vehicle accident analyzer 102, as depicted in FIG. 1, or may be implemented within separate servers and/or separate computing environments. For instance, a deduplication component 120, a model execution engine 122 and/or a library of the trained ML models 104 may be implemented in a public, private, or hybrid cloud in a cloud computing environment, or may be implemented in an on-premise data center associated with the vehicle accident analyzer 102.

At operation 602, the vehicle accident analyzer 102 may receive data associated with an accident involving one or more vehicles. In various examples, the accident-related data received in operation 602 may be an initial reporting of a vehicle accident within an initial set of accident data, or may be new or updated accident data for a previously reported accident. Examples of the accident-related data that may be received in operation 602 can include statements, reports, and/or other information provided by the parties or witnesses to the accident. Additional examples of accident-related data can include data reports or statements from medical providers, first responders, insurance representatives, etc., and may include transcripts of written or recorded statements made by the parties involved or witnesses to an accident. Further examples of accident data may include the vehicle specifications, vehicle telematics data, image or video data associated with the accident, and/or the driving conditions associated with the accident.

At operation 604, the vehicle accident analyzer 102 may determine whether to immediately invoke or to delay execution of one or more ML model(s) 104 configured to determine an injury probability for the accident based on the accident-related data. In some instances, operation 604 may be performed by a deduplication component 120. As described above, the deduplication component 120 may implement delay timers and/or event buffers to control the timing and conditions under which the ML models 104 may be executed. When the vehicle accident analyzer 102 receives the accident-related data in operation 602, the deduplication component 120 may analyze the accident data, using an accident event processor component 306 or similar component. In various examples, the deduplication component 120 may identify the type of the accident data received in operation 602, the data source from which the accident data was received, and/or the relative timing of the accident data compared to other receipts of accident data. Based on one or more of the attributes of the accident data received in operation 602, the deduplication component 120 may determine in operation 604 whether to immediately execute an ML model 104 based on the received accident data (604: No), or whether to implement a timer to delay or defer execution of the ML model 104 (604: Yes).

At operation 606, the vehicle accident analyzer 102 may instantiate a delay timer 308 to delay or defer execution of an ML model 104 until after the completion of the delay timer 308. For instance, the deduplication component 120 may determine that the accident data received in operation 602 is unlikely to significantly change the injury probability output by the ML model(s) 104, and/or that there is a likelihood that additional accident data will be received for the same accident in the near future. As a result, the deduplication component 120 may instantiate a delay timer 308 in operation 606 and/or may store the accident data received in operation 602 into an event buffer 310. When the delay timer 308 completes, the accident data received in operation 602 (and any additional new or updated accident data) may be cleared from the event buffer 310 and stored into the vehicle accident data store 114, after which the deduplication component 120 may invoke the model execution engine 122 to execute (or re-execute) the ML model(s) 104 for the accident.

At operation 608, the vehicle accident analyzer 102 may determine and/or retrieve a data payload of accident-related to provide as input to one or more selected ML model(s) 104. As noted above, a data payload may include a set of accident-related data provided as input to an ML model 104. Different ML models 104 may have different payload data corresponding to different combinations of accident-related input data. In some examples, the model training engine 118 may provide payload information for each ML model 104 to the model execution engine 122, which may use the payload information to generate payloads for the executing ML model(s) 104. For instance, a payload of model input data may include a combination of data fields based on the accident-related data received in operation 602 and additional (e.g., previously received) accident-related data for the same accident, which may be retrieved from the vehicle accident data store 114.

At operation 610, the vehicle accident analyzer 102 may execute the selected ML model(s) 104 to determine the injury probabilities associated with the accident. In some examples, the vehicle accident analyzer 102 may use a model execution engine 122 configured to execute the selected ML model(s) 104, provide as input to the models the payload(s) determined in operation 608, and then receive outputs from the models includes injury probabilities associated with the accident. In some examples, one or more of the ML model(s) 104 may include decision tree models. In such examples, the model execution engine 122 may be configured to traverse the branches of the decision tree model, evaluating each branching criteria based on the accident data, and reaching a leaf node having an associated injury probability value. In other examples, the ML models 104 may include neural network-based models and/or other machine learning models, in which the payload may be provided to the input layer of the neural network.

At operation 612, the vehicle accident analyzer 102 may determine one or more target entities and/or target systems associated with the accident. For instance, the target entities associated with a vehicle accident may include the parties to the accident, witnesses, medical providers, law enforcement, and/or insurance providers associated with the parties. The target systems may include any computing systems or devices associated with these entities, such as medical provider servers, law enforcement servers, insurance provider systems, client devices of the parties to the accident, etc. In various examples, determining the target systems may include determining the client device identifiers, server or domain names or identifiers, web portal addresses associated with the target entities, and the like.

At operation 614, the vehicle accident analyzer 102 may compare the injury probability of the accident, determined based on the model output operation 610, to one or more probability thresholds associated with the target systems determined in operation 612. As discussed above, the vehicle accident analyzer 102 may determine and store various probability thresholds associated with target systems and/or particular processes to be invoked on the target systems. Based on the injury probability associated with the accident, and the various injury probabilities of a particular target system, the vehicle accident analyzer 102 may determine which processes (if any) to invoke on the target system. As an example, an injury probability for an accident that is greater than a probability threshold (614: Yes) may cause the vehicle accident analyzer 102 to initiate a process on a target system in operation 616. In contrast, an injury probability for the accident that is less than the probability threshold (614: No) may cause the vehicle accident analyzer 102 not to initiate the process, after which the process 600 may proceed back to operation 612 to determine a next potential target system associated with the same accident.

At operation 616, the vehicle accident analyzer 102 may determine and initiate the process(es) on the target system determined in operation 612. As discussed above, the processes initiated on the target systems 126-132 may include notifications, messages, web service invocations, API calls, and the like, any or all of which may cause processing tasks to be executed in the selected target system. For instance, based on determining that an injury probability associated with an accident exceeds a probability threshold, the vehicle accident analyzer 102 may initiate a process via a party (or third-party) client device to provide additional accident data for the ML models 104. Additional processes that can be initiated on the target systems 126-132 may include instantiating alerts/notifications and/or other user interfaces instructing a party to seek medical care, or to complete additional electronic forms relating to law enforcement, insurance claim processing, etc. Further examples of processes that can be initiated on various target systems 126-132 in operation 616 may include automated requests to schedule medical exams and/or initiate medical procedures, automated uploading of accident-related information directly to medical care provider systems, opening and/or modifying insurance claims automatically on a target system, automatically routing claims internally within an insurance provider to a specific claim-handling group or representative, and/or initiating secure uploads of relevant accident data from the vehicle accident data store 114 and/or data sources 106-110 to one or more target system(s) 130.

Figure 7:
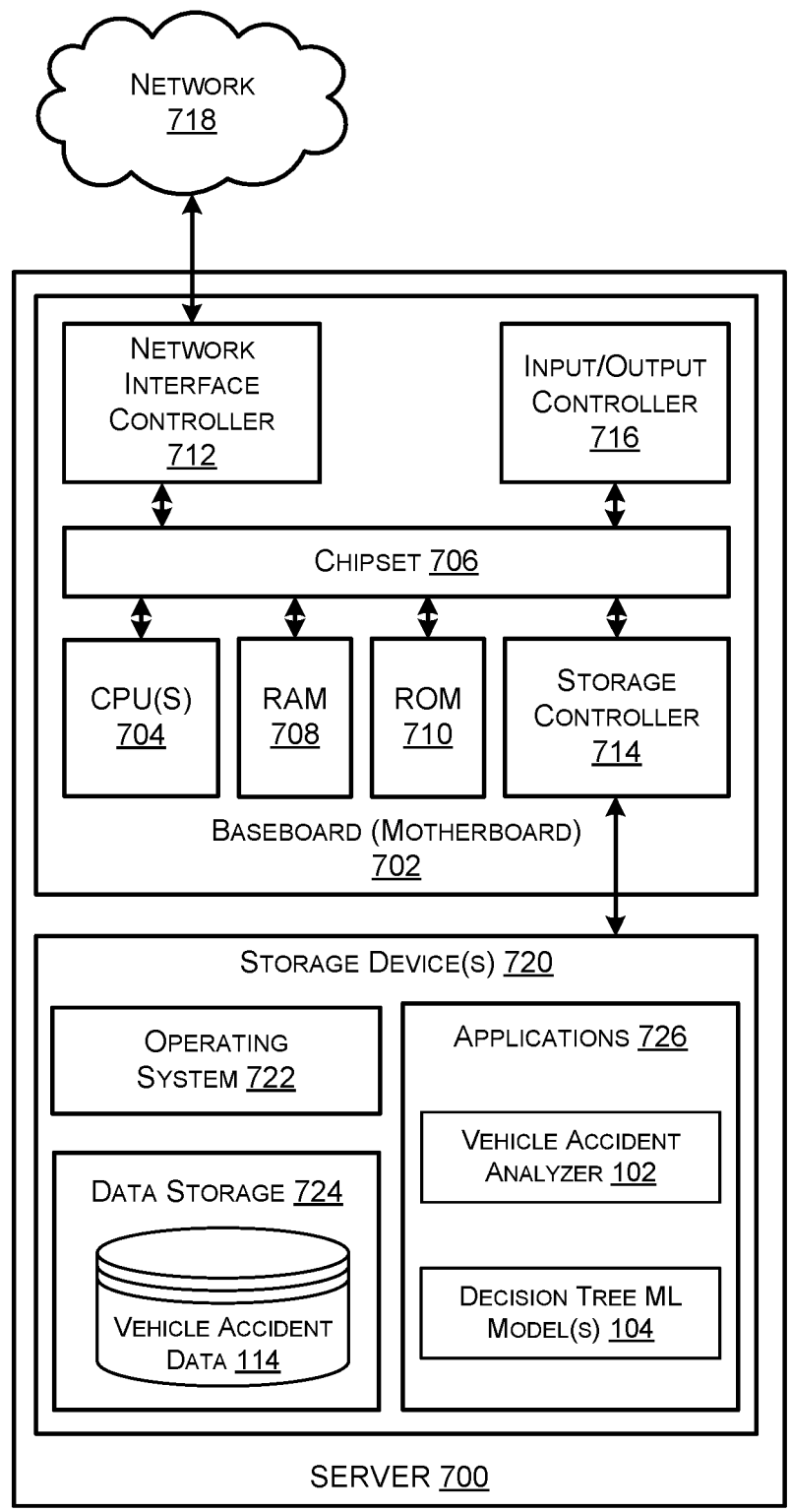
FIG. 7 is an example architecture of a computer server capable of executing program components for implementing various techniques described herein.

FIG. 7 shows an example architecture of a computer server 700 capable of executing program components for implementing the various functionality described herein. Although the computer architecture in this example is labeled as a server, it can be understood from this disclosure that similar or identical computer architectures may be implemented via workstations, desktop or laptop computers, tablet computers, network appliances, mobile devices (e.g., smartphones, etc.) or other computing devices, and/or virtual machines or cloud-based computing solutions, any or all of which may execute any combination of the software components described herein. The server 700 may, in some examples, correspond to any of the computing systems or devices described above, such as a vehicle accident analyzer 102 including decision tree models 104 and/or vehicle accident data store 114, data source systems 106-110, target systems 126-132, and/or any other computing devices, systems, or components executing the software components described herein. It will be appreciated that in various examples described herein, a server 700 might not include all of the components shown in FIG. 7, may include additional components that are not explicitly shown in FIG. 7, and/or may utilize a different architecture from that shown in FIG. 7.

The server 700 includes a baseboard 702, or "motherboard," which may be a printed circuit board to which a multitude of components or devices are connected by way of a system bus or other electrical communication paths. In one illustrative configuration, one or more central processing units ("CPUs") 704 operate in conjunction with a chipset 706. The CPUs 704 can be standard programmable processors that perform arithmetic and logical operations necessary for the operation of the server 700.

The CPUs 704 perform operations by transitioning from one discrete, physical state to the next through the manipulation of switching elements that differentiate between and change these states. Switching elements generally include electronic circuits that maintain one of two binary states, such as flip-flops, and electronic circuits that provide an output state based on the logical combination of the states of one or more other switching elements, such as logic gates. These basic switching elements can be combined to create more complex logic circuits, including registers, adders-subtractors, arithmetic logic units, floating-point units, and the like.

The chipset 706 provides an interface between the CPUs 704 and the remainder of the components and devices on the baseboard 702. The chipset 706 can provide an interface to a RAM 708, used as the main memory in the server 700. The chipset 706 can further provide an interface to a computer-readable storage medium such as a ROM 710 or non-volatile RAM ("NVRAM") for storing basic routines that help to startup the server 700 and to transfer information between the various components and devices. The ROM 710 or NVRAM can also store other software components necessary for the operation of the server 700 in accordance with the configurations described herein.

The server 700 can operate in a networked environment using logical connections to remote computing devices and computer systems through a network, such as the network 718, which may be similar or identical to any of the communication networks discussed above. The chipset 706 also may include functionality for providing network connectivity through a Network Interface Controller (NIC) 712, such as a gigabit Ethernet adapter. The NIC 712 is capable of connecting the server 700 to other computing devices (e.g., operator devices, external software development environments, test systems, cloud-based deployment systems, etc.) over the network 718. It should be appreciated that multiple NICs 712 can be present in the server 700, connecting the computer to other types of networks and remote computer systems. In some instances, the NICs 712 may include at least on ingress port and/or at least one egress port.

The server 700 can also include one or more input/output controllers 716 for receiving and processing input from a number of input devices, such as a keyboard, a mouse, a touchpad, a touch screen, an electronic stylus, or other type of input device. Similarly, an input/output controller 716 can provide output to a display, such as a computer monitor, a flat-panel display, a digital projector, a printer, or other type of output device.

The server 700 can include one or more storage device(s) 720, which may be connected to and/or integrated within the server 700, that provide non-volatile storage for the server 700. The storage device(s) 720 can store an operating system 722, data storage systems 724, and/or applications 726, which may include any or all of the systems and/or components described herein. The storage device(s) 720 can be connected to the server 700 through a storage controller 714 connected to the chipset 706. The storage device(s) 720 can consist of one or more physical storage units. The storage controller 714 can interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The server 700 can store data on the storage device(s) 720 by transforming the physical state of the physical storage units to reflect the information being stored. The specific transformation of physical state can depend on various factors, in different embodiments of this description. Examples of such factors can include, but are not limited to, the technology used to implement the physical storage units, whether the storage device(s) 720 are characterized as primary or secondary storage, and the like.

For example, the server 700 can store information to the storage device(s) 720 by issuing instructions through the storage controller 714 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The server 700 can further read information from the storage device(s) 720 by detecting the physical states or characteristics of one or more particular locations within the physical storage units.

In addition to the storage device(s) 720 described above, the server 700 can have access to other computer-readable storage media to store and retrieve information, such as program modules, data structures, or other data. It should be appreciated by those skilled in the art that computer-readable storage media is any available media that provides for the non-transitory storage of data and that can be accessed by the server 700. In some examples, the various operations performed by the computing systems described herein (e.g., vehicle accident analyzer 102, data sources systems 106-110, target systems 126-132, etc.) may be implemented within a datacenter including one or more servers or devices similar to server 700. For instance, some or all of the operations described herein may be performed by one or more server 700 operating in a networked (e.g., client-server or cloud-based) arrangement.

By way of example, and not limitation, computer-readable storage media can include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

As mentioned briefly above, the storage device(s) 720 can store an operating system 722 utilized to control the operation of the server 700. In some examples, the operating system 722 comprises a LINUX operating system. In other examples, the operating system 722 comprises a WINDOWS® SERVER operating system from MICROSOFT Corporation of Redmond, Washington. In further examples, the operating system 722 can comprise a UNIX operating system or one of its variants. It should be appreciated that other operating systems can also be utilized. The storage device(s) 720 can store other system or application programs and data utilized by the server 700.

In various examples, the storage device(s) 720 or other computer-readable storage media is encoded with computer-executable instructions which, when loaded into the server 700, transform the computer from a general-purpose computing system into a special-purpose computer capable of implementing various techniques described herein. These computer-executable instructions transform the server 700 by specifying how the CPUs 704 transition between states, as described above. In some examples, the server 700 may have access to computer-readable storage media storing computer-executable instructions which, when executed by the server 700, perform the various techniques described herein. The server 700 can also include computer-readable storage media having instructions stored thereupon for performing any of the other computer-implemented operations described herein.

As illustrated in FIG. 7, the storage device(s) 720 may store one or more data storage systems 724 configured to store data structures and other data objects. In some examples, data storage systems 724 may include one or more data stores, which may be similar or identical to the vehicle accident data store 114 and/or even data stores associated with any number of the data sources 106-110.

Additionally, the software applications 726 stored on the server 700 may include one or more client applications, services, and/or other software components. For example, application(s) 726 may include any combination of the components 110-118 and 124 discussed above in relation to the vehicle accident analyzer 102, and/or other software components described above in reference to FIGS. 1-6.

Figure 8:
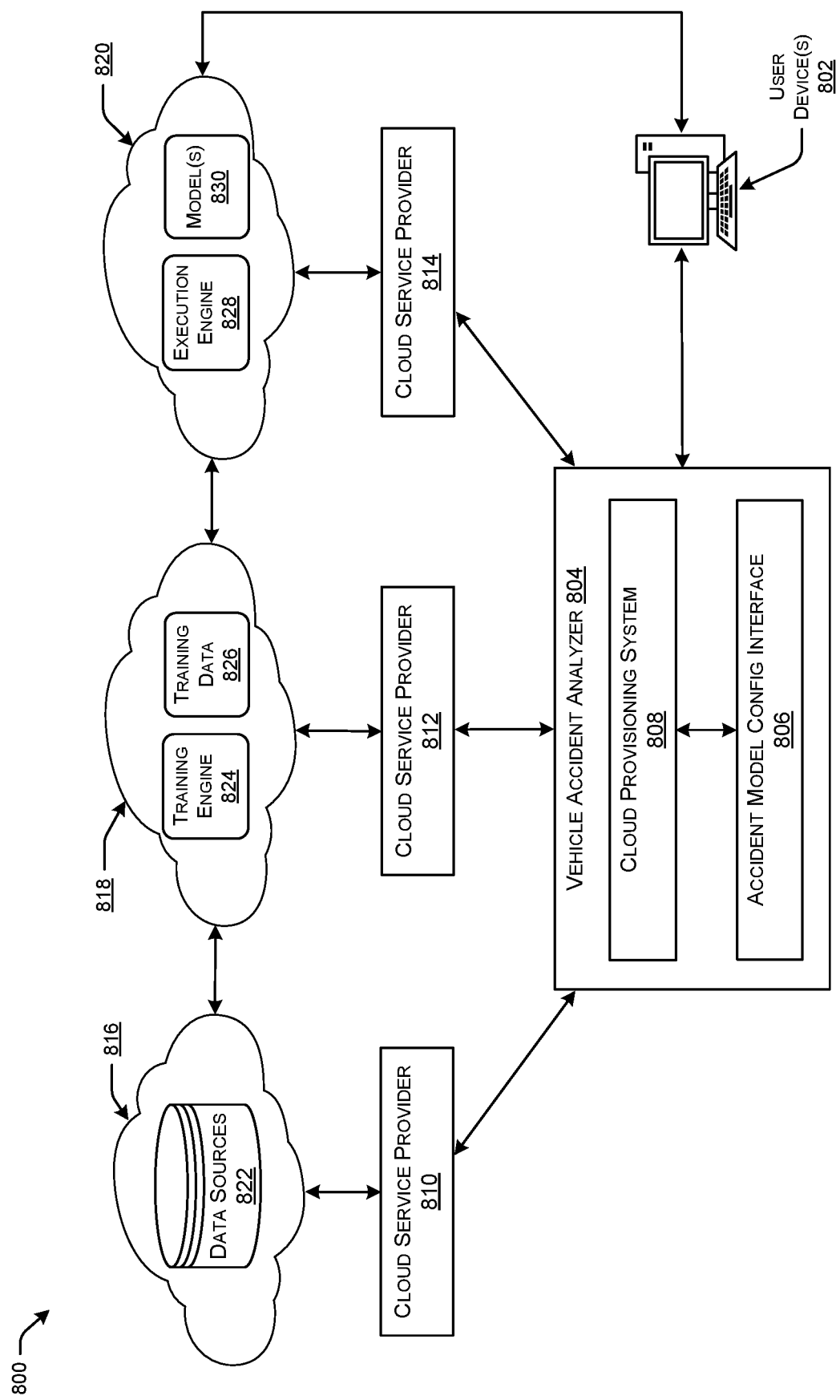
FIG. 8 depicts an example computing environment including a vehicle accident analyzer configured to create and deploy cloud-based systems for training and/or executing machine learning models for vehicle accident analysis, in accordance with one or more examples of the present disclosure.

As discussed above, the various techniques described herein for training and executing machine learning models configured to determine injury probabilities based on vehicle accident data, can be implemented within various different computing environments. In some examples, one or both of a model training engine and/or model execution engine as described herein may operate in a cloud-based environment (e.g., a public cloud, private cloud, and/or hybrid cloud environment) and/or in a separate non-cloud computing environment (e.g., an on-premise datacenter). FIG. 8 depicts one example of a cloud-based computing environment 800 for training and executing models to determine injury probabilities based on vehicle accident data.

In this example, the computing environment 800 includes one or more user devices 802 associated with an organization for which cloud environments are to be created, provisioned, and managed. The user devices 802 may be controlled by a deployment engineer or other operator associated with the organization and may be implemented using, for example, a desktop or laptop computer, tablet computer, mobile device, or any other computing device. The user devices 802 may include network interfaces and functionality capable of accessing the vehicle accident analyzer 804, and/or client software configured to access interface(s) provided by the vehicle accident analyzer 804 or cloud-based applications and service. The vehicle accident analyzer 804 in this example may be similar or identical to the vehicle accident analyzer 104 described in the above examples, and may be implemented using various different computing architectures, including one or more computing devices, servers, and/or other computing systems. Additionally, as shown in this example, the vehicle accident analyzer 804 may include various computing components to provide one or more interface(s), receive accident model configuration variables from the user devices 802, and to create and deploy cloud-based systems via cloud service providers.

In this example, the vehicle accident analyzer 804 includes an accident model configuration interface 806 and a cloud provisioning system 808: however, the vehicle accident analyzer 804 also may include any other components or features described herein for vehicle accident analyzer 104. In this example, the accident model configuration interface 806 may be accessible by the user devices 802 and/or other authorized client devices associated with the organization. In some examples, the user devices 802 may execute a thin, web-based client (e.g., Internet browser) to access the accident model configuration interface 806 via a secure network. Additionally or alternatively, the accident model configuration interface 806 may include a thick client in which some or all of the interface functionality may execute on the user devices 802. The accident model configuration interface 806 may include a graphical user interface (GUI), such as web browser-based or application-based interface through which a user or operator may provide data relating to the constructing, training, and execution of models as described herein for determining the potential injury probabilities associated with vehicle accidents. In some examples, a GUI need not be implemented and the accident model configuration interface 806 may correspond to a programmatic interface (e.g., API) or other non-graphical interface.

The accident model configuration interface 806 may include any interface through which the vehicle accident analyzer 804 receives one or more configuration data, including configuration data relating to the models to be trained and executed, and/or cloud environment configuration data (e.g., configuration variables) from an operator of the organization. For instance, such configuration variables may include any data associated with a configuration (and/or any other attribute) of a cloud deployment. For instance, configuration variables may include any selection made by operator or any input provided during the creation, configuration, and/or deployment of a cloud environment. Examples of configuration variables may include, but are not limited to, account names and/or alias associated with the environment, the organizations and/or projects associated with the environment, and contact information associated with the environment (e.g., administrator(s), email addresses, etc.). Additional examples of configuration variables may include the type/functionality of the environment (e.g., production or non-production), and roles associated with the account (e.g., identification of administrators, product developers, etc.). Additional configuration variables may include the specifications for network constructs to be used in the environment, such as the IP addresses and/or configuration data of the virtual private network, routing tables, routing rules, security policies/groups, and/or network access controllers associated with the environment. Additional examples of configuration variables may include data identifying the cloud service provider and/or cloud region for the environment, the continuous integration and continuous deployment (CI/CD) pipeline associated with the environment, the encryption component(s) to be used within the environment, the logging component(s) to be used, and/or any other automation components tools, or services to be used in the environment. It can be understood from the context of this disclosure that the examples of configuration variables described herein are illustrative and non-limiting, and that any attribute of a cloud deployment/environment may be represented as configuration variable in some examples.

It can be understood in the context of this disclosure that different configuration data may be used to create and deploy different types of models for determining potential injury probabilities associated with vehicle accidents, including models trained using different training data sources, different sets of model training/testing data, and/or different model training algorithms. Additional configuration data received via the accident model configuration interface 806 may be used to determine the execution parameters for such models, including the input data types, delay timers, etc. In some examples different cloud environments may be associated with different organizations. For instance, the vehicle accident analyzer 804 may provide different customized interfaces for different operators and/or user devices 802, which are configured to receive vehicle accident model configuration variables based on the organization for which the new cloud-based deployment (e.g., a model training or model execution deployment) is requested. Different organizations may have different predetermined sets of variable configuration data, and/or provide different interfaces to users. For instance, an organization may be associated with a same set of administrators and/or may requires all cloud deployments to be created via the same cloud service provider(s).

The data received via the accident model configuration interface 806 may include any of the data described herein relating to training and/or executing machine learning models configured to determine injury probabilities based on vehicle accident data. After receiving the data, the vehicle accident analyzer 804 may determine and deploy one or more cloud-based systems to perform any or all of the functionalities of the model training engine and/or model execution engine as described herein. In some examples, organizations may store and use pre-existing templates defining the specifications of new cloud-based environments for training and executing vehicle accident analysis models for the organization. For instance, cloud environment templates may include software instructions that can be directly executed by a cloud provisioning system. For instance, templates may be stored as configuration files (e.g., infrastructure as code (IaC) configuration files) which may be executable and/or used by executable software to create and provision cloud environments.

As shown in this example, the cloud provisioning system 808 may be used to create and configure the requested cloud-based deployments for training and/or executing the various vehicle accident analysis models described herein. The cloud provisioning system 808 using one or more cloud service providers 810-814 to deploy various systems within the corresponding clouds 816-820. In some examples, the cloud provisioning system 808 may access and/or generate a storage space (e.g., a repository) for templates and/or other executable files corresponding to the requested cloud deployments of vehicle accident analyzer models. A repository for cloud-based systems may store a combination of the variabilized template(s) generated based on the configuration data received from the user devices 802, as well as additional non-variabilized templates associated with the organization, the project, the environment type, and/or the cloud service provider. In some examples, a repository may be associated with a particular project or product development team, and different sub-folders (or other sub-spaces) within the repository may store templates for different environments (e.g., a production environment, various test environments, various research environments, etc.) associated with the project or product development team.

A requested deployment of a cloud-based systems may include deployments of model training systems and/or model execution systems for vehicle accident analyzer models. In this example, each of the vehicle accident-related data sources 822, model training engine 824, model training data 826, model execution engine 828, and/or trained ML models 830 may be similar or identical to the corresponding components discussed in above examples. Although in this example, each of the components 822-830 stored and/or deployed within the cloud-based environment 800 is depicted as residing in a single cloud, it can be understood that certain components (e.g., the model training engine and/or model execution engine) may be deployed across multiple different clouds in some instances. To provision any or all of these cloud-based deployments, the cloud provisioning system 808 may determine and transmit cloud provisioning instructions to the appropriate cloud service providers 810-814. Such instructions may include infrastructure as code software instructions using a declarative configuration language in a structured format. To generate and execute vehicle accident analysis models in cloud-based environments, the vehicle accident analyzer 804 may use languages including one or more of Terraform® by Hashicorp®, Cloudformation® by AWS®, Azure Resource Manager® by Microsoft Azure®, Cloud Deployment Manager® by Google®, Oracle Orchestration Cloud® by Oracle®, or Ansible® by Redhat®. It can be understood from this disclosure that these structured format languages are non-limiting examples only, and that any other domain-specific language for provisioning cloud deployments may be used in other examples.

As illustrated by the various examples above, the techniques described herein provide a number of technical advantages in operating vehicle accident analysis systems, and more generally in training and executing machine learning models in event-based computing infrastructures. Initially, the examples of training and executing machine learning models described herein provide improvements over existing systems by more quickly and accurately identifying potentially injured parties based on vehicle accident data. The machine learning models described herein, including but not limited to decision tree models with branching criteria based on vehicle accident data and injury ground truth data, may determine more accurate probability predictions for accident injuries, based on payloads that include combined data from various data sources. As a result, the vehicle accident analysis systems described herein may improve overall vehicle safety and individual health outcomes when vehicle accidents occur, by detecting potential injuries earlier and more accurately than existing systems, even in situations when the injuries may be unreported, concealed, and/or unknown to the other parties involved in the accident. These systems and techniques also include improved and more efficient routing of potential injury notifications and relevant accident data to medical care providers, enabling the injured parties to receive the appropriate medical care more quickly than with existing systems. Similarly, these techniques enable improved prioritization and triage of potential injuries based on the likelihood and severity of the injuries, and also may more effectively determine false positives among the potential injuries (e.g., inaccurate injury data, exaggerated and/or unrelated injury reports).

The techniques described herein also may improve the functioning and efficiency of computer systems that include execution engines for machine learning models. As described herein, a model execution engine may be integrated with an event-driven system in which data events are received including updates to accident data records, and in which the data events may trigger an execution (or re-execution) of the corresponding trained model. Based on the types of accident data events, the timing of the received events, and/or the data sources from which the events are received, the vehicle accident analysis system may implement various delay timers that control the timing of a subsequent execution of the model. For instance, the vehicle accident analysis system can be configured to automatically re-execute a trained model and determine updated model output (e.g., an updated injury probability) in response to unique or significant changes to the data associated with a vehicle accident, but may delay and defer performing a re-execution of the model in response to duplicate events and/or insignificant data changes. Accordingly, the deduplication component and delay timers described above can be configured to save computational resources and provide improved efficiency by optimally determining when and how often the machine learning model is to be re-executed in response to receiving updated data events. Further, the improvements described herein for model execution engines apply not only to the machine learning models configured to predict injury probabilities associated with vehicle accidents, but may similarly apply to any number of additional machine learning models having various structures and algorithms and configured to perform predictive modeling in any number of different technical fields.

Additionally or alternatively, these techniques may provide improvements in the technical fields of device and/or server monitoring and workload management. As described above, a vehicle accident analysis system may evaluate and apply injury probability thresholds for routing communications and providing processing instructions to various target systems. These probability thresholds may be adjusted dynamically based on the current workloads and/or current available resources at each target system. The vehicle accident analysis system may determine optimal probability thresholds for each target system in order to distribute the numbers and types of tasks initiated on the target systems, and to control the corresponding processing loads handled by the target systems. Coordinated configuration of the probability thresholds for the various target systems may improve the efficiency of routing various downstream processing tasks to an optimal target system, as well as providing a workload control mechanism to manage and coordinate the processing workload across multiple target systems which may be unknown to one another.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

While the invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A computer-implemented method, comprising:
   receiving, by a computer system and from a first data source, data associated with a vehicle accident;
   determining, based on at least one of the data associated with the vehicle accident or the first data source, a delayed model execution time associated with a machine learning decision tree model;
   receiving, by the computer system and at a time prior to the delayed model execution time, second data associated with the vehicle accident; generating, by the computer system, a data payload based at least in part on the first data and the second data;
providing, by the computer system and at a time corresponding to the delayed model execution time, the data payload as input to the machine learning decision tree model;
determining, by the computer system, an injury probability associated with the vehicle accident, based at least in part on an output from the machine learning decision tree model;
determining, by the computer system, a target computer system of an entity associated with the vehicle accident, based at least in part on the injury probability associated with the vehicle accident; and
transmitting, by the computer system, an instruction to the target computer system to initiate a process.

2. The computer-implemented method of claim 1, wherein the first data associated with the vehicle accident includes at least one of:
a statement from a party involved in the vehicle accident;
location coordinates associated with the vehicle accident;
weather conditions associated with the vehicle accident; or
telematics data captured by a vehicle involved in the vehicle accident.

3. The computer-implemented method of claim 1, wherein
determining the delayed model execution time comprises:
determining, based at least in part on a first data channel through which the first data was received, a model execution delay time;
initiating a timer based at least in part on the model execution delay time; and
executing the machine learning decision tree model based at least in part on a completion of the timer, wherein executing the machine learning decision tree model includes providing the data payload as input to the machine learning decision tree model.

4. The computer-implemented method of claim 1, wherein determining the target computer system comprises:
determining a workload metric associated with the target computer system, at a time associated with receiving the data;
determining a probability threshold based at least in part on the workload metric;
comparing the probability threshold to the injury probability; and
determining the target computer system as a target for the instruction, based at least in part on determining that the injury probability meets or exceeds the probability threshold.

5. The computer-implemented method of claim 1, wherein the machine learning decision tree model includes:
a plurality of decision tree branches;
a separate injury probability associated with each of the plurality of decision tree branches; and
a plurality of branching criteria associated with the plurality of decision tree branches, wherein the plurality of branching criteria are determined during training.

6. The computer-implemented method of claim 5, wherein the plurality of branching criteria of the machine learning decision tree model includes:
a first branching criteria based on a keyword within an accident description from the first data source; and
a second branching criteria based on data received from a second data source different from the first data source.

7. The computer-implemented method of claim 6, wherein the second data source comprises at least one of:
a location data source;
a weather data source;
a road conditions data source; or
an image or video data source associated with a location of the vehicle accident.

8. The computer-implemented method of claim 1, further comprising:
determining, after receiving the first data associated with the vehicle accident, a likelihood that additional data from an additional data source is expected to be received within a threshold time;
determining, based on the likelihood, to delay the execution of the machine learning decision tree model; and
initiating a delay timer including an expiration time based on the threshold time.

9. The computer-implemented method of claim 8, further comprising, after initiating the delay timer:
receiving additional data associated with the vehicle accident; and
storing the additional data in an event buffer; and
in response to determining that the expiration time of the delay timer has been reached:
moving the additional data from the event buffer into a modified data payload; and
executing the machine learning decision tree model based on the modified data payload.

10. The computer-implemented method of claim 1, wherein determining the delayed model execution time associated with the machine learning decision tree model comprises:
determining a likelihood of additional accident-related data being received during a future time period.

11. The computer-implemented method of claim 1, wherein determining the delayed model execution time associated with the machine learning decision tree model comprises:
determining a relative time between when the vehicle accident occurred and when the first data associated with the vehicle accident was received from the first data source.

12. A computer system, comprising:
one or more processors; and
one or more non-transitory computer-readable media storing computer-executable instructions that, when executed by the one or more processors, cause the one or more processors to perform operations comprising:
receiving, from a first data source and via a first data channel, first data associated with a vehicle accident;
determining, based on at least one of the first data associated with the vehicle accident or the first data source, a delayed model execution time associated with a machine learning decision tree model;
receiving, at a time prior to the delayed model execution time, second data associated with the vehicle accident;
retrieving, from an accident data store, previous data associated with the vehicle accident;
generating a payload based at least in part on the first data and the second data associated with the vehicle accident and the previous data associated with the vehicle accident;
executing the machine learning decision tree model at a time corresponding to the delayed model execution time, the executing comprising providing the payload as input to the machine learning decision tree model;

determining an injury probability associated with the vehicle accident, based at least in part on an output from the machine learning decision tree model;

determining a target computer system of an entity associated with the vehicle accident, based at least in part on the injury probability; and transmitting an instruction to the target computer system to initiate a process.

13. The computer system of claim 12, wherein the first data associated with the vehicle accident includes at least one of:

a statement from a party involved in the vehicle accident;
location coordinates associated with the vehicle accident;
weather conditions associated with the vehicle accident; or
telematics data captured by a vehicle involved in the vehicle accident.

14. The computer system of claim 12, wherein the machine learning decision tree model includes a branching criteria based on at least one of:

a party to the vehicle accident associated with the first data channel;
a time associated with receiving the first data, relative to a time of the vehicle accident; or
a keyword within a description from a party of the vehicle accident.

15. The computer system of claim 12, the operations further comprising:

determining an attribute associated with the vehicle accident, wherein the attribute includes at least one of:
geographic region associated with the vehicle accident;
a time period associated with the vehicle accident; or
a driving condition associated with the vehicle accident; and
selecting the machine learning decision tree model from a plurality of models, based at least in part on the attribute.

16. The computer system of claim 12, wherein determining the delayed model execution time comprises:

determining, based at least in part on the first data channel, a model execution delay time;
initiating a timer based at least in part on the model execution delay time; and
executing the machine learning decision tree model based at least in part on a completion of the timer, wherein executing the machine learning decision tree model includes providing a data payload as input to the machine learning decision tree model.

17. The computer system of claim 12, wherein determining the target computer system comprises:

determining a workload metric associated with the target computer system, at a time associated with receiving the first data;
determining a probability threshold based at least in part on the workload metric;
comparing the probability threshold to the injury probability; and
determining the target computer system as a target for the instruction, based at least in part on determining that the injury probability meets or exceeds the probability threshold.

18. One or more non-transitory computer-readable media storing instructions executable by a processor, wherein the instructions, when executed by the processor, cause the processor to perform operations comprising:

receiving, from a first data source and via a first data channel, first data associated with a vehicle accident;
determining, based on at least one of the first data associated with the vehicle accident or the first data source, a delayed model execution time associated with a machine learning decision tree model;
receiving, at a time prior to the delayed model execution time, via a second data channel different from the first data channel, second data associated with the vehicle accident;
determining input data based at least in part on the first data and the second data;
providing the input data as input to the machine learning decision tree model at a time corresponding to the delayed model execution time;
determining an injury probability associated with the vehicle accident, based at least in part on an output from the machine learning decision tree model;
determining a target computer system of an entity associated with the vehicle accident, based at least in part on the injury probability; and
transmitting an instruction to the target computer system to initiate a process associated with the vehicle accident.

19. The one or more non-transitory computer-readable media of claim 18, wherein determining the delayed model execution time comprises:

determining, based at least in part on the first data channel, a model execution delay time;
initiating a timer based at least in part on the model execution delay time; and
executing the machine learning decision tree model based at least in part on a completion of the timer, wherein executing the machine learning decision tree model includes providing the input data as input to the machine learning decision tree model.

20. The one or more non-transitory computer-readable media of claim 18, wherein determining the target computer system comprises:

determining a workload metric associated with the target computer system, at a time associated with receiving the first data;
determining a probability threshold based at least in part on the workload metric;
comparing the probability threshold to the injury probability; and
determining the target computer system as a target for the instruction, based at least in part on determining that the injury probability meets or exceeds the probability threshold.

* * * * *